(12) United States Patent
Faris et al.

(10) Patent No.: US 12,070,441 B2
(45) Date of Patent: Aug. 27, 2024

(54) MONOGLYCERIDE USE IN ANIMALS

(71) Applicant: CAN TECHNOLOGIES, INC., Wayzata, MN (US)

(72) Inventors: Richard Joel Faris, Nowthen, MN (US); Junmei Zhao, Maple Grove, MN (US)

(73) Assignee: CAN TECHNOLOGIES, INC., Wayzata, MN (US)

( * ) Notice: Subject to any disclaimer, the term of this patent is extended or adjusted under 35 U.S.C. 154(b) by 608 days.

(21) Appl. No.: 17/270,760

(22) PCT Filed: Aug. 27, 2019

(86) PCT No.: PCT/US2019/048264
§ 371 (c)(1),
(2) Date: Feb. 23, 2021

(87) PCT Pub. No.: WO2020/046879
PCT Pub. Date: Mar. 5, 2020

(65) Prior Publication Data
US 2021/0251940 A1     Aug. 19, 2021

Related U.S. Application Data

(60) Provisional application No. 62/724,979, filed on Aug. 30, 2018.

(51) Int. Cl.
*A61K 31/231* (2006.01)
*A23K 20/158* (2016.01)
(Continued)

(52) U.S. Cl.
CPC .......... *A61K 31/231* (2013.01); *A23K 20/158* (2016.05); *A23K 50/30* (2016.05);
(Continued)

(58) Field of Classification Search
CPC .. A61K 31/231; A61K 9/0056; A23K 20/158; A23K 50/30; A23K 50/60; A61P 3/02; A23V 2250/192
See application file for complete search history.

(56) References Cited

U.S. PATENT DOCUMENTS

2004/0062847 A1*  4/2004  Koike ................... A21D 2/165
                                                           426/601
2018/0077951 A1*  3/2018  Jansen ................. A23K 20/158
(Continued)

FOREIGN PATENT DOCUMENTS

CN       106605782 A  *  5/2017
CN       106605782 A       5/2017
(Continued)

OTHER PUBLICATIONS

Hansen et al., '2-Oleoy! Glycerol Is a GPR119 Agonist and Signals GLP-1 Release in Humans', The Journal of Clinical Endocrinology & Metabolism, vol. 96, issue 9, 2011, p. E1409-E1417. (Year: 2011).*
(Continued)

*Primary Examiner* — Deborah D Carr

(57) ABSTRACT

Various embodiments relate to monoglyceride use in animals such as post-weaning pigs. A method of feeding an animal includes feeding the animal a diet comprising one or more monoglycerides. Various embodiments provide concentrates, premixes, top dresses, or complete feeds for carrying out the method and methods of making the same.

14 Claims, 6 Drawing Sheets

(51) Int. Cl.
　　　A23K 50/30　　　(2016.01)
　　　A23K 50/60　　　(2016.01)
　　　A61K 9/00　　　(2006.01)
　　　A61P 3/02　　　(2006.01)
(52) U.S. Cl.
　　　CPC ............ *A23K 50/60* (2016.05); *A61K 9/0056* (2013.01); *A61P 3/02* (2018.01)

(56)　　　　　　References Cited

U.S. PATENT DOCUMENTS

| | | |
|---|---|---|
| 2019/0075824 A1 | 3/2019 | Yun |
| 2021/0251940 A1 | 8/2021 | Faris |

FOREIGN PATENT DOCUMENTS

| | | | |
|---|---|---|---|
| EP | 1342419 A1 * | 9/2003 | ........... A23K 20/158 |
| EP | 1342419 A1 | 9/2003 | |
| EP | 3020284 B1 | 9/2018 | |
| EP | 3843554 A1 | 7/2021 | |
| KR | 20050046845 A | 5/2005 | |
| KR | 101719598 B1 | 3/2017 | |
| WO | 2018053286 A1 | 3/2018 | |
| WO | 2020046879 A1 | 3/2020 | |

OTHER PUBLICATIONS

Hansen et al., "2-Oleoyl Glycerol Is a GPR119 Agonist and Signals GLP-1 Release in Humans", The Journal of Clinical Endocrinology & Metabolism, vol. 96, issue 9, Sep. 1, 2011 (Sep. 1, 2011), p. E1409-E1417.

* cited by examiner

MONOGLYCERIDE USE IN ANIMALS

CROSS-REFERENCE TO RELATED APPLICATIONS

This application is a national phase application of PCT/US2019/048264, filed Aug. 27, 2019, and entitled MONOGLYCERIDE USE IN ANIMALS, which claims the benefit of U.S. Provisional Patent Application No. 62/724,979, filed Aug. 30, 2018, and entitled MONOGLYCERIDE USE IN ANIMALS, each of which is hereby incorporated by reference in its entirety.

BACKGROUND

Weaning is a challenging time in a young pig's life. "In the wild" pigs are naturally weaned from their mothers at about 8 weeks of age. However, in conventional farming, pigs are weaning around 3 weeks of age, but could be slightly younger or older. There are several stressors that cause challenge during weaning such as changes in social hierarchy, separation from mother, changes in feed presentation (e.g, milk versus meal or pellet), changes in feed composition (e.g., milk versus cereal and protein sources), and new environments that can bring disease pressure. These challenges are compounded by an underdeveloped immune system and a still stabilizing gut microbial profile.

Transient anorexia is an important nutritional phenomenon that often occurs during the weaning of pigs. Weaning is often accompanied by transient anorexia. Some pigs will starve out for several day before eating. Additionally, it takes one to two weeks to return to pre-weaning dry matter intake. This is a large growth check on performance. However, more than performance should be considered. During periods of anorexia, the intestine undergoes atrophy which decreases barrier function of the intestine. In large part this is due to nutrient interaction with receptors in the intestine that cause secretion of intestinal peptides that control growth and maintenance of the intestine. This disruption of barrier function due to poor post-weaning intake can cause increase morbidity and mortality by allowing increased intestinal permeability to bacteria and potential toxins.

Another nutritional phenomenon of the weaning of pigs is poor use of lipids. Prior to weaning, the main energy source of pigs comes from lipid in the milk and is used not only for maintenance energy, but to increase the fat deposition from its low levels at birth. However, post-weaning lipids are poorly used by the pig even with the comparably low quantity of fat supplied in post-weaning diets. Moreover, there is a negative relationship between circulating triglycerides post-weaning and performance of the pig, demonstrating a negative energy balance through mobilization of stored lipid but also a potential a challenge with the nutritional use of triglycerides post-weaning.

Strategies to improve post-weaning intake in pigs can lead to better end of nursery weight and potentially reduce morbidity, mortality, and veterinary treatments. The use of fat in improving post-weaning performance has often been a focus of improving post-weaning performance because of the high amount of fat in sow's milk. This work has focused on the use of emulsifiers or anti-caking agents to improve fat digestibility. However, this improvement in fat digestibility does not consistently lead to improvements in post-weaning intake and gain in young pigs.

SUMMARY OF THE INVENTION

Various embodiments provide a method of feeding an animal. The method includes feeding the animal a diet including one or more monoglycerides.

Various embodiments provide a method of feeding a post-weaning pig. The method includes feeding the post-weaning pig a diet including one or more monoglycerides including oleate (C18:1). The diet increases the activation of GPR119 receptors in the pig, to increase average daily feed intake (ADFI), and to increase average daily gain (ADG). The C18:1 monoglycerides are about are about 0.01 wt % to about 5 wt % of the animal's diet, of a daily feed ration fed to the animal, or a combination thereof.

Various embodiments provide a concentrate, premix, or top dress for animals that includes one or more monoglycerides including oleate (C18:1), wherein the weight ratio of C18:1 monoglycerides to C18:0 and C16:0 monoglycerides is at least about 0.01, such as about 0.01 to about 20, or about 0.01 to about 0.6.

Various embodiments provide a complete feed for animals including the concentrate, premix, or top dress combined with a base animal feed. The one or more monoglycerides including oleate (C18:1) are about 0.01 wt % to about 5 wt % of the complete feed. Various embodiments provide a method of making the complete feed, including combining the premix, concentrate, or top dress with the base animal feed to form the complete feed.

In various embodiments, the present invention provides certain advantages over other compositions for feeding animals and methods of using the same, at least some of which are unexpected. For example, in various embodiments, the composition and method of the present invention provides greater average daily gain (ADG) post-weaning, fewer veterinary treatments post-weaning, increased growth of intestinal villi, improved health, reduced mortality and decreased removals post-weaning (e.g., improved survivability), or a combination thereof, as compared to a method that is otherwise the same but includes feeding the animal less or different proportions of the one or more monoglycerides. In various embodiments, the one or monoglycerides in the composition and method of the present invention increase insulin secretion in the subject animal. In various embodiments, the one or more monoglycerides in the composition and method of the present invention decrease blood glucose (e.g., in response to increased insulin), decrease blood triglycerides, or a combination thereof. In various embodiments, the one or more monoglycerides in the composition and method of the present invention increases activation of GPR119 receptors in the animal. In various embodiments, by causing increased activated of GPR119 receptors, increasing insulin, decreasing blood glucose, decreasing blood triglycerides, increasing growth of intestinal villi, or a combination thereof, the composition or method of the present invention can provide increased growth and food intake as compared to other similar compositions or methods that include less or different proportions of the one or more monoglycerides. In various embodiments, the one of more monoglycerides improves processability, such as by acting as an emulsifier, and can improve pelleting parameters.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
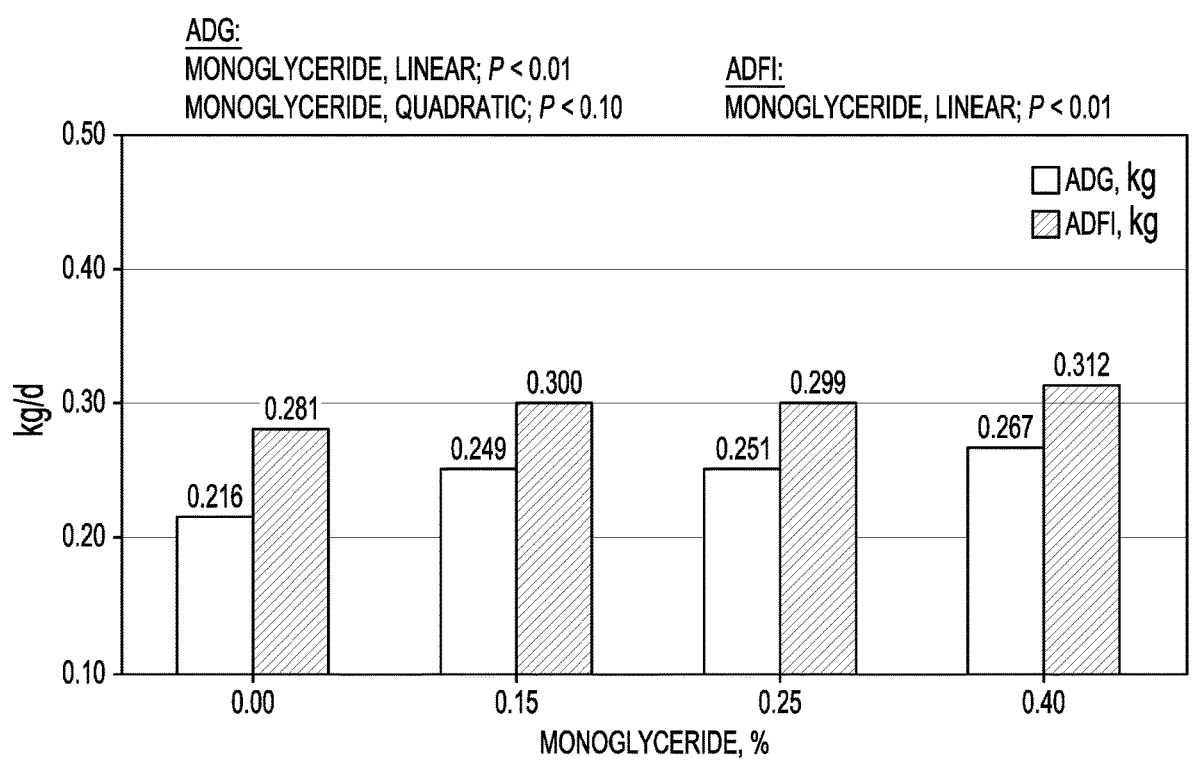
FIG. 1 illustrates ADG and ADFI versus percent monoglyceride for various weaning pigs, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Method of Feeding an Animal.

In various embodiments the present invention provides a method of feeding an animal. The method includes feeding the animal a diet including one or more monoglycerides. The method can cause greater average daily feed intake (ADFI), greater average daily gain (ADG), fewer veterinary treatments, reduced mortality and decreased removals, or a combination thereof, as compared to a method that is otherwise the same but includes feeding the animal less of the one or more monoglycerides. The method is not limited to any particular mechanism of action. The one or more monoglycerides can increase insulin secretion in the animal, decreasing blood glucose and blood triglycerides. The one or more monoglycerides can increase activation of GPR119 receptors in the animal, such as in the intestine.

The method can be a method of managing the animal, such as managing the effects of weaning, decreased intake or gain, decreased insulin production, increased blood triglycerides, increased blood glucose, decreased activation of GFP119 receptors, or a combination thereof, such as in a post-weaned animal. The method can be a method of treating decreased average daily feed intake (ADFI) or decreased average daily gain (ADG). The method is a method of increasing insulin secretion, decreasing blood glucose, decreasing blood triglycerides, increasing activation of GPR119 receptors, or a combination thereof.

The one or more monoglycerides can be given to the animal in any one or more suitable edible medium. For example, a complete feed, a concentrate, a premix, a top dress, or a combination thereof, can provide the one or more monoglycerides in the animal's diet. The complete feed can be a daily feed ration that is fed to the animal on most days or on all days, such as on a regular or ad lib schedule.

The animal can be any suitable animal at any suitable age such that the animal benefits from the diet including the one or more monoglycerides. The animal is not human. The animal can be a ruminant, pig, poultry, horse, aquaculture, or wild game. The animal can be a pig, such as a domestic pig, *Sus scrofa domesticus*. The domestic animal can be a breed of domestic pig including Aksai Black Pied, American Yorkshire, Angeln Saddleback, Appalachian English, Arapawa Island, Auckland Island Pig, Australian Yorkshire, Ba Xuyen, Babi Kampung, Bangur Pig, Bantu, Basque, Bazna, Beijing Black, Belarus Black Pied, Belgian Landrace, Bengali Brown Shannaj, Bentheim Black Pied, Berkshire, Bisaro, Black Canarian Pig, Black Slavonian, Breitovo, British Landrace, British Lop, British Saddleback, Bulgarian White, Cantonese, Celtic Pig, Chato Murciano, Chester White, Chiangmai Blackpig, Moodum Chiangmai, Creole Pig, Cumberland Pig, Czech Improved White, Danish Landrace, Danish Protest Pig, Dermantsi Pied, Dharane Kalo Sungur, Duroc, Dutch Landrace Pig, East Balkan Pig, Essex, Estonian Bacon, Fengjing Pig, Finnish Landrance, Forest Mountain, French Landrace, Gascon, German Landrace, Gloucestershire Old Spot, Grice, Guinea Hog, Göttingen Minipig, Hampshire, Hante, Hereford, Hezuo, Hogan Hog, Huntingdon Black Hog, Iberian, Italian Landrace, Japanese Landrace, Jeju Black Pig, Jinhua Pig, Juliana, Kakhetian, Kele Pig, Kemerovo, Korean Native Pig, Krskopolje, Kunekune, Lacombe, Large Black, Large Black-White, Large White, Latvian White, Leicoma, Li Yan Pig, Lincolnshire Curly-Coated Pig, Linderödssvin, Lithuanian Native, Lithuanian White, Livny, Malhado De Alcobaça, Mangalitsa, Meishan, Middle White, Minokawa Buta, Minzhu, Mong Cai, Mora Romagnola, Moura, Mukota, Mulefoot, Murom, Myrhorod, Neijiang, Nero Dei Nebrodi, Ningxiang, North Caucasian, North Siberian, Norwegian Landrace, Norwegian Yorkshire, Ossabaw Island, Oxford Sandy and Black, Pakchong 5, Philippine Native, Pietrain, Poland China, Red Wattle, Semirechensk, Siberian Black Pied, Small Black, Small White, Spots, Surabaya Babi, Swabian-Hall, Swedish Landrace, Taihu Pig, Tamworth, Thuoc Nhieu, Tibetan, Tokyo-X, Tsivilsk, Turopolje, Ukrainian Spotted Steppe, Ukrainian White Steppe, Urzhum, Vietnamese Potbelly, Welsh, Wessex Saddleback, West French White, Windsnyer, Wuzishan, Yanan, Yorkshire Blue and White, or a combination thereof.

The animal can be any suitable age. For example, the animal can be weaning, post-weaning, or a combination thereof. As used herein, "weaning" specifies that the animal has been taken from its mother and is no longer allowed to drink its mother's milk. As used herein, "post-weaning" specifies that the animal has been weaned from its mother but has not yet reached an age where it is ready to leave the nursery. In some embodiments, the method can be used from the onset of weaning or post-weaning to the end of nursery. A weaning or post-weaning pig can be a pig that is about 1 week to about 15 weeks old, or about 3 weeks to about 9 weeks old, or less than, equal to, or greater than about 1 week, 2 weeks, 3, 4, 5, 6, 7, 8, 9, 10, 11, 12, 13, 14 weeks, or about 15 weeks old or more. A post-weaning pig can be a pig that has stopped feeding from its mother but has not yet reached an age suitable to leave the nursery, for example, is less than or equal to about 9 weeks to 15 weeks, such as less than or equal to about 9 weeks, 10, 11, 12, 13, 14, or about 15 weeks old. The method can be used for a pig that is from birth to about 9 to about 15 weeks old, or from about birth, 1 week, 2 weeks, 3, 4, 5, 6, 7, or from about 8 weeks to about less than or equal to about 9 weeks, 10, 11, 12, 13, 14, or about 15 weeks old.

The one or more monoglycerides can form any suitable proportion of the animal's overall diet such that the method performs as described herein. The one or more monoglycerides are at least about 0.01 wt % of the animal's diet, of a daily feed ration fed to the animal, or a combination thereof, or about 0.01 wt % to about 10 wt %, 0.1 wt % to about 1%, about 0.2 wt % to about 0.4 wt %, or about 0.01 wt % or less, or less than, equal to, or more than about 0.05 wt %, 0.1, 0.15, 0.2, 0.25, 0.3, 0.35, 0.4, 0.45, 0.5, 0.6, 0.7, 0.8, 1, 1.2, 1.4, 1.6, 1.8, 2, 2.5, 3, 4, 5, 6, 8, or about 10 wt % or more of the animal's diet, of a daily feed ration fed to the animal, or a combination thereof. The animal can be a pig and the one or more monoglyerides can be about 20 to about 500 mg per kg of the pig's mass per day, or about 40 to about 250 mg per kg of the pig's mass per day, or about 20 mg or less, or less than, equal to, or greater than about 30 mg, 40, 50, 60, 70, 80, 90, 100, 120, 140, 160, 180, 200, 220, 240, 260, 280, 300, 350, 400, 450, or about 500 mg per kg of the pig's mass per day (about 5 kg) or more. During weaning and post-weaning, pigs can have wide variation in the amount of food eaten per day.

The animal's diet can include or be substantially free of soy oil, palm oil, tallow, animal fat, vegetable fat, coconut oil, fish oil, lecithin, diglycerides, triglycerides, or any combination thereof. In various embodiments, the animal's diet, a daily feed ration fed to the animal including the one or more monoglycerides, or a combination thereof, can be substantially free of or can include soy oil, palm oil, tallow, animal fat, vegetable fat, coconut oil, fish oil, lecithin, diglycerides, triglycerides, or any combination thereof. The animal's feed ration, the animal's diet, or a combination thereof, can be substantially free of or can include antimicrobial monoglycerides (e.g., monoglycerides having fatty acid resides of C12:0 or less).

As used herein, the term "monoglyceride" refers to a monoacylglycerol, which is an ester that can be formed between a single fatty acid and glycerol, such as at the 1-position of the glycerol, the 2-position, or a combination thereof. The one or more monoglycerides can be chosen from glycerol propionate (propanoate, C3:0), butyrate (butanoate, C4:0), valerate (pentanoate, C5:0), caproate (hexanoate, C6:0), enanthate (heptanoate, C7:0), caprylate (octanoate, C8:0), pelargonate (nonanoate, C9:0), caprate (decanoate, C10:0), undecylate (undecanoate, C11:0), laurate (dodecanoate, C12:0), tridecylate (tridecanoate, C13:0), myristate (tetradecanoate, C14:0), pentadecylate (pentadecanoate, C15:0), palmitate (hexadecanoate, C16:0), margarate (heptadecanoate, C17:0), stearate (octadecenoate, C18:0), nonadecylate (nonadecanoate, C19:0), arachidate (eicosanoate, C20:0), heneicosylate (heneicosanoate, C21:0), behenate (docosanoate, C22:0), tricosylate (tricosanoate, C23:0), lignocerate (tetracosanoate, C24:0), pentacosylate (pentacosanoate, C25:0), cerotate (hexacosanoate, C26:0), heptacosylate (heptacosanoate, C27:0), montanate (octacosanoate, C28:0), nonacosylate (nonacosanoate, C29:0), melissate (triacontanoate, C30:0), henatriacontylate (henatriacontanoate, C31:0), lacceroate (dotriacontanoate, C32:0), psyllate (tritriacontanoate, C33:0), geddate (tetratriacontanoate, C34:0), ceroplastate (pentatriacontanoate, C35:0), hexatriacontylate (hexatriacontanoate, C36:0), heptatriacontanoate (heptatriacontanoate, C37:0), octatriacontanoate (octatriacontanoate, C38:0), α-linolenate (C18:3), stearidonate (C18:4), eicosapentaenoate (C20:5), docosahexaenoate (C22:6), linoleate (C18:2), linolelaidate (C18:2), γ-linolenate (C18:3), dihomo-γ-linolenate (C20:3), arachidonate (C20:4), docosatetraenoate (C22:4), palmitoleate (C16:1), vaccenate (C18:1), paullinate (C20:1), oleate (C18:1), elaidate (C18:1), gondoate (C20:1), erucate (C22:1), nervonate (C24:1), mead acid ester (C20:3), and a combination thereof. The one or more monoglycerides can include or exclude any one or more monoglyceride members from the list in this paragraph. The one or more monoglycerides can be non-antimicrobial or can be free of fatty acid residues less than or equal to C12:0. The one or more monoglycerides can be free of or can include fatty acid residues less than or equal to C9:0, C10:0, C11:0, C12:0, C13:0, or C14:0, or any combination thereof. The one or more monoglycerides can be chosen from glycerol stearate, palmitate, oleate, linoleate, laurate, and a combination thereof.

The one or more monoglycerides used can have any suitable source with any suitable purity prior to becoming part of a premix, concentrate, a top dress, or complete feed that is part of the animal's diet. The source can be a natural and unpurified source or can be an enhanced source having a monoglyceride concentration or distribution not found naturally. For example, the monoglycerides in the animal's diet, prior to combining with one or more optional other materials to form a premix, concentrate, top dress, or complete feed that provides the one or more monoglycerides in the animal's diet, can independently be provided with a purity of about 85 wt % to about 100 wt %, or about 90 wt % to about 95 wt %, or about 85 wt % or less, or less than, equal to, or greater than about 86%, 87, 88, 89, 90, 91, 92, 93, 94, 95, 96, 97, 98, 99, 99.9, or about 99.99 wt % or more.

One or more monoglycerides including stearate (octadecenoate, C18:0) can be about 0 wt % to about 5 wt % of the animal's diet, of a daily feed ration fed to the animal, or a combination thereof, or about 0.05 wt % to about 0.6 wt %, or about 0 wt %, or less than, equal to, or greater than about 0.01 wt %, 0.02, 0.03, 0.04, 0.05, 0.06, 0.08, 0.1, 0.15, 0.2, 0.25, 0.3, 0.35, 0.4, 0.45, 0.5, 0.55, 0.6, 0.65, 0.7, 0.8, 0.9, 1, 1.5, 2, 2.5, 3, 3.5, 4, 4.5, or about 5 wt % or more.

One or more monoglycerides including oleate (C18:1) can be about 0 wt % to about 5 wt % of the animal's diet, of a daily feed ration fed to the animal, or a combination thereof, or about 0.01 wt % to about 0.3 wt %, about 0.02 wt % to about 0.25 wt %, or about 0 wt %, or less than, equal to, or greater than 0.01 wt %, 0.02, 0.04, 0.06, 0.08, 0.1, 0.12, 0.14, 0.16, 0.18, 0.2, 0.22, 0.24, 0.25, 0.26, 0.28, 0.3, 0.35, 0.4, 0.45, 0.5, 0.6, 0.7, 0.8, 0.9, 1, 1.5, 2, 2.5, 3, 3.5, 4, 4.5, or about 5 wt % or more.

The one or more monoglycerides including palmitate (hexadecanoate, C16:0) can be about 0 wt % to about 5 wt % of the animal's diet, of a daily feed ration fed to the animal, or a combination thereof, or about 0.01 wt % to about 0.25 wt %, or about 0 wt %, or less than, equal to, or greater than about 0.01 wt %, 0.02, 0.04, 0.06, 0.08, 0.1, 0.12, 0.14, 0.16, 0.18, 0.2, 0.22, 0.24, 0.25, 0.3, 0.35, 0.4, 0.45, 0.5, 0.6, 0.7, 0.8, 0.9, 1, 1.5, 2, 2.5, 3, 3.5, 4, 4.5, or about 5 wt % or more.

The animal's diet, a daily feed ration fed to the animal, or a combination thereof, can have a weight ratio of C18:1 monoglycerides to C16:0 monoglycerides of about 0 to about 20, or about 2 to about 3.5, or about 0, or less than, equal to, or greater than about 0.01, 0.1, 0.2, 0.4, 0.6, 0.8, 1, 1.2, 1.4, 1.6, 1.8, 2, 2.1, 2.2, 2.3, 2.4, 2.5, 2.6, 2.7, 2.8, 2.9, 3, 3.0, 3.1, 3.2, 3.3, 3.4, 3.5, 4, 5, 6, 8, 10, 12, 14, 16, 18, or about 20 or more.

The animal's diet, a daily feed ration fed to the animal, or a combination thereof, can have a weight ratio of C18:1 monoglycerides to C18:0 monoglycerides of about 0 to about 20, or about 0.01 to about 0.7, or about 0, or less than, equal to, or greater than about 0.01, 0.05, 0.1, 0.15, 0.2, 0.25, 0.3, 0.35, 0.4, 0.45, 0.5, 0.55, 0.6, 0.65, 0.7, 0.8, 0.9, 1, 1.5, 2, 2.5, 3, 3.5, 4, 4.5, 5, 6, 8, 10, 12, 14, 16, 18, or about 20 or more.

The animal's diet, a daily feed ration fed to the animal, or a combination thereof, can have a weight ratio of C18:1 monoglycerides to C18:0 and C16:0 monoglycerides of about 0 to about 20, about 0.01 to about 0.6, or about 0, or less than, equal to, or greater than about 0.01, 0.05, 0.1, 0.15, 0.2, 0.25, 0.3, 0.35, 0.4, 0.45, 0.5, 0.55, 0.6, 0.7, 0.8, 0.9, 1, 1.5, 2, 2.5, 3, 3.5, 4, 4.5, 5, 6, 7, 8, 10, 12, 14, 16, 18, or about 20 or more.

The animal's diet, a daily feed ration fed to the animal, or a combination thereof, can further include or can be free of antimicrobials, antibiotics, a zinc additive, or a combination thereof. Zinc additives such as zinc oxide are common mineral supplement included at pharmacological doses in weaning and post-weaning pigs to improve health and performance, and can be used at any suitable concentration, such as about 2,000 to about 4,000 ppm of the animal's diet or of a daily feed ration given to the animal.

Concentrate, Premix, Top Dress, or Complete Feed.

Various embodiments of the present invention provide a concentrate, premix, or top dress for animals that includes the one or more monoglycerides that can be used to perform embodiments of the method of the present invention. A concentrate is composition that can include high-protein feed components and can also include vitamins, minerals, appropriate medications, and combinations thereof. A concentrate is typically 5-40% of the diet but can be higher or lower. A concentrate can include additives. Concentrates can be used to make complete feeds by adding available grains or other energy sources. Premixes are compositions that can include vitamins, minerals, appropriate medications, carriers, and combinations thereof, and are typically less than 1% of the diet but can be higher. The carrier can increase bulk to improve distribution in compounding to prepare a more complete feed material. Examples of carriers can include soy mill run, rice bran, and similar edible plant by-products. Such premixes can be used to formulate concentrates and complete feeds. A top dress is a supplement added at specific time intervals to the animal ration to provide a specific supplement or supplements over a period of time that makes it inconvenient or difficult to include in complete feed.

Concentrates, premixes, and top dresses can be offered to the animal alone or compounded with other materials. The concentrate or premix can be for use with ruminants, pigs, poultry, equine animals, aquaculture, wild game, or a combination thereof. The concentrate or premix can be for pigs, such as for weaning and post-weaning pigs.

The concentrate, premix, or top dress can have a weight ratio of C18:1 monoglycerides to C16:0 monoglycerides of about 0 to about 20, or about 2 to about 3.5, or about 0, or less than, equal to, or greater than about 0.01, 0.1, 0.2, 0.4, 0.6, 0.8, 1, 1.2, 1.4, 1.6, 1.8, 2, 2.1, 2.2, 2.3, 2.4, 2.5, 2.6, 2.7, 2.8, 2.9, 3, 3.0, 3.1, 3.2, 3.3, 3.4, 3.5, 4, 5, 6, 8, 10, 12, 14, 16, 18, or about 20 or more.

The concentrate, premix, or top dress can have a weight ratio of C18:1 monoglycerides to C18:0 monoglycerides of about 0 to about 20, or about 0.01 to about 0.7, or about 0, or less than, equal to, or greater than about 0.01, 0.05, 0.1, 0.15, 0.2, 0.25, 0.3, 0.35, 0.4, 0.45, 0.5, 0.55, 0.6, 0.65, 0.7, 0.8, 0.9, 1, 1.5, 2, 2.5, 3, 3.5, 4, 4.5, 5, 6, 8, 10, 12, 14, 16, 18, or about 20 or more.

The concentrate, premix, or top dress can have a weight ratio of C18:1 monoglycerides to C18:0 and C16:0 monoglycerides of about 0 to about 20, about 0.01 to about 0.6, or about 0, or less than, equal to, or greater than about 0.01, 0.05, 0.1, 0.15, 0.2, 0.25, 0.3, 0.35, 0.4, 0.45, 0.5, 0.55, 0.6, 0.7, 0.8, 0.9, 1, 1.5, 2, 2.5, 3, 3.5, 4, 4.5, 5, 6, 7, 8, 10, 12, 14, 16, 18, or about 20 or more.

Various embodiments of the present invention provide a complete feed for animals. The complete feed includes the one or more monoglycerides and can be used to perform embodiments of the method of the present invention. The complete feed can include an embodiment of the concentrate, premix, or top dress described herein that includes the one or more monoglycerides. The complete feed also includes a base animal feed. A complete feed is a nutritionally adequate feed for animals that is compounded to be fed as the sole ration and is capable of maintaining life and/or promoting production without any additional substance being consumed except water. Complete feeds are compounded mixtures containing all the nutrients of concentrates plus various energy sources such as grains, some fat, and the like. In addition, certain major minerals may be added. An example of a complete feed can include cottonseed meal, rapeseed and canola meals, meat and bone meal, wheat middlings, soybean meal, corn gluten meal, distillers grains, blood meal, salt, macro-minerals, minerals, vitamins, and combinations thereof.

The complete feed can be ruminant feed, pig feed, poultry feed, equine feed, aquaculture feed, wild game feed, or a combination thereof. The complete feed can be a pig feed composition. The complete feed can be a pig feed for weaning pigs. The complete feed can be in any suitable form, such as in the form of a pellet, a mash, an extruded food, an expanded food, or a combination thereof.

About 0 wt % to about 5 wt % of the complete feed can be one or more monoglycerides including stearate (octadecenoate, C18:0), or about 0.05 wt % to about 0.6 wt %, or about 0 wt %, or less than, equal to, or greater than about 0.01 wt %, 0.02, 0.03, 0.04, 0.05, 0.06, 0.08, 0.1, 0.15, 0.2, 0.25, 0.3, 0.35, 0.4, 0.45, 0.5, 0.55, 0.6, 0.65, 0.7, 0.8, 0.9, 1, 1.5, 2, 2.5, 3, 3.5, 4, 4.5, or about 5 wt % or more.

About 0 wt % to about 5 wt % of the complete feed can be one or more monoglycerides including oleate (C18:1), or about 0.01 wt % to about 0.3 wt %, about 0.02 wt % to about 0.25 wt %, or about 0 wt %, or less than, equal to, or greater than 0.01 wt %, 0.02, 0.04, 0.06, 0.08, 0.1, 0.12, 0.14, 0.16, 0.18, 0.2, 0.22, 0.24, 0.25, 0.26, 0.28, 0.3, 0.35, 0.4, 0.45, 0.5, 0.6, 0.7, 0.8, 0.9, 1, 1.5, 2, 2.5, 3, 3.5, 4, 4.5, or about 5 wt % or more.

About 0 wt % to about 5 wt % of the complete feed can be one or more monoglycerides including palmitate (hexadecanoate, C16:0), or about 0.01 wt % to about 0.25 wt %, or about 0 wt %, or less than, equal to, or greater than about 0.01 wt %, 0.02, 0.04, 0.06, 0.08, 0.1, 0.12, 0.14, 0.16, 0.18, 0.2, 0.22, 0.24, 0.25, 0.3, 0.35, 0.4, 0.45, 0.5, 0.6, 0.7, 0.8, 0.9, 1, 1.5, 2, 2.5, 3, 3.5, 4, 4.5, or about 5 wt % or more.

The complete feed can have a weight ratio of C18:1 monoglycerides to C16:0 monoglycerides of about 0 to about 20, or about 2 to about 3.5, or about 0, or less than, equal to, or greater than about 0.01, 0.1, 0.2, 0.4, 0.6, 0.8, 1, 1.2, 1.4, 1.6, 1.8, 2, 2.1, 2.2, 2.3, 2.4, 2.5, 2.6, 2.7, 2.8, 2.9, 3, 3.0, 3.1, 3.2, 3.3, 3.4, 3.5, 4, 5, 6, 8, 10, 12, 14, 16, 18, or about 20 or more.

The complete feed can have a weight ratio of C18:1 monoglycerides to C18:0 monoglycerides of about 0 to about 20, or about 0.01 to about 0.7, or about 0, or less than, equal to, or greater than about 0.01, 0.05, 0.1, 0.15, 0.2, 0.25, 0.3, 0.35, 0.4, 0.45, 0.5, 0.55, 0.6, 0.65, 0.7, 0.8, 0.9, 1, 1.5, 2, 2.5, 3, 3.5, 4, 4.5, 5, 6, 8, 10, 12, 14, 16, 18, or about 20 or more.

The complete feed can have a weight ratio of C18:1 monoglycerides to C18:0 and C16:0 monoglycerides of about 0 to about 20, about 0.01 to about 0.6, or about 0, or less than, equal to, or greater than about 0.01, 0.05, 0.1, 0.15, 0.2, 0.25, 0.3, 0.35, 0.4, 0.45, 0.5, 0.55, 0.6, 0.7, 0.8, 0.9, 1, 1.5, 2, 2.5, 3, 3.5, 4, 4.5, 5, 6, 7, 8, 10, 12, 14, 16, 18, or about 20 or more.

Method of Making Complete Feed, Concentrate, or Top Dress.

A method of making a complete feed can include combining an embodiment of the premix, concentrate, or top dress described herein that includes the one or more monoglycerides with a base animal feed to form the complete feed.

A method of making a concentrate or top dress can include combining an embodiment of the premix described herein that includes the one or more monoglycerides with a source of protein to form the concentrate or top dress.

The combining can be performed in any suitable way. In some embodiments, the one or more monoglycerides can provide emulsification properties that improve mixing.

EXAMPLES

Various embodiments of the present invention can be better understood by reference to the following Examples which are offered by way of illustration. The present invention is not limited to the Examples given herein.

As can be seen from the titles of some of the Examples, the connection between monoglycerides and benefits to post-weaning piglets was initially noticed in studies that were not attempting to find this effect. The percentages reported are weight percentages unless otherwise indicated. As used herein, a low zinc diet is about 150 ppm or less, and a high zinc diet is 150 to 4000 ppm and usually 2000 to 4000 ppm.

Example 1. Effect of Monoglyceride on Performance

A 42-day trial (experimental diets feed for 21 days) with initial body weight of 6.7 kg contained treatments with and without monoglyceride in diets with pharmacological ZnO. Inclusion of monoglyceride increased 0-21 day gain and intake by 6.1 and 3.6%, respectively. At the end of the 42-day trial pigs were 0.8 kg heavier. Monoglyceride purity was >90% and fatty acid profile is in Table 2 as Example 1.

Example 2. Effect of Monoglyceride on Intake and Gain

A 42-day trial with initial body weight of 6.2 kg contained treatments with and without monoglyceride in diets with pharmacological ZnO. Inclusion of monoglyceride increased 0-22 day gain and intake dose dependently. The largest improvements were at 0.25% inclusion increasing intake and gain from 0-22 days by 18.6 and 19.1%, respectively. Monoglyceride was included at 0, 0.25, 0.5, and 1.0% of the diet. The monoglyceride was >90% purity and is Example 2 in Table 1. Additional data was collected in the trial from pelleting the diets and it appeared that inclusion of monoglycerides decreased pelleting amps (i.e., energy needed to pellet the diet).

Example 3. Effect of Monoglycerides on Piglet Performance

A 42-day trial with initial body weight of 7.1 kg contained a control and three monoglycerides. The first monoglyceride was a monoglyceride that is >90% purity and the fatty acid profile is Example 3 in Table 2. The second monoglyceride is a glycerol monolaurate that is >90% glycerol monolaurate. The third monoglyceride was a glycerol monostearate that is 85% monoglyceride, 10% diglyceride, and 2% triglyceride. The fatty acid profile for the second two monoglycerides in not presented in Table 2 under Example 3. The objective of the trial was to determine the effect of monoglycerides on performance. Diets were low ZnO. Monoglycerides only marginally improved relative performance and a difference could not be distinguished between them. In this trial in the second and third week monoglycerides did statistically improve performance, but not in the first week or the final 3 weeks.

Example 4. Effect of Monoglyceride with Changes in Fatty Acid Saturation

A 42-day trial with initial body weight of 6.1 kg contained monoglyceride at 0.25% and was tested in diets with high ZnO. The monoglyceride was >90% and the fatty acid profile is presented in Table 2, as Example 4. A marginal decrease in performance was found with monoglyceride inclusion. Evidence of improved pelleting parameters, such as decreased hot pellet temperature, amps, and pellet hardness, were found with inclusion of monoglyceride.

Example 5. Evaluation of the Effects of Monoglycerides with or without Medium Chain Triglycerides (MCT) on Growth Performance and Health Status of Nursery Pigs A 42-day trial with initial body weight of 5.4 kg used doses of 0, 0.15, 0.25, and 0.4% monoglyceride. The monoglyceride was >90% purity and the fatty acid profile is presented in Table 2 as Example 5. The diets contained antibiotics and high ZnO. Antibiotics were delivered to the water line to deliver a specific dose per liter as needed in the trial. Monoglyceride increased ADG and ADFI with increasing dose from 0-21 days post-weaning. The best treatment increased gain and intake by 23.6 and 11%, respectively. Inclusion of monoglyceride also dose-dependently decreased mortalities, mortality+removal, and injectable treatment during the 42-day trial. The trial was a 2×4 factorial. MCFA (Palm Kernel Oil) was a factor that may or may not have caused a difference in the effect of the monoglycerides. There was some difference in mortality and removals, and injectable treatments with and without MCFA in the diets. Monoglyceride was more responsive to dose when MCFA was not included. However, one additional different trial detected no interaction between MCFA and monoglycerides.

FIG. 1 illustrates ADG and ADFI versus percent monoglyceride inclusion.

Figure 2A:
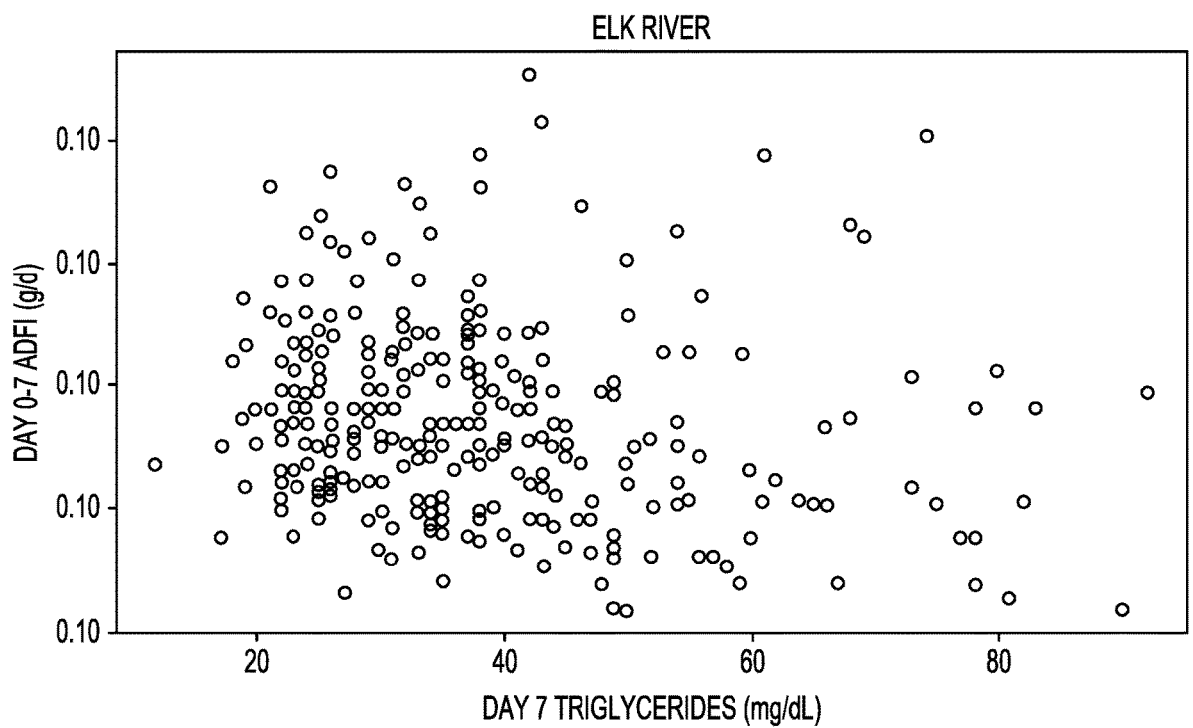
FIG. 2A illustrates day 0-8 ADFI versus day 7 triglyceride concentration for various weaning pigs, in accordance with various embodiments.
Figure 2B:
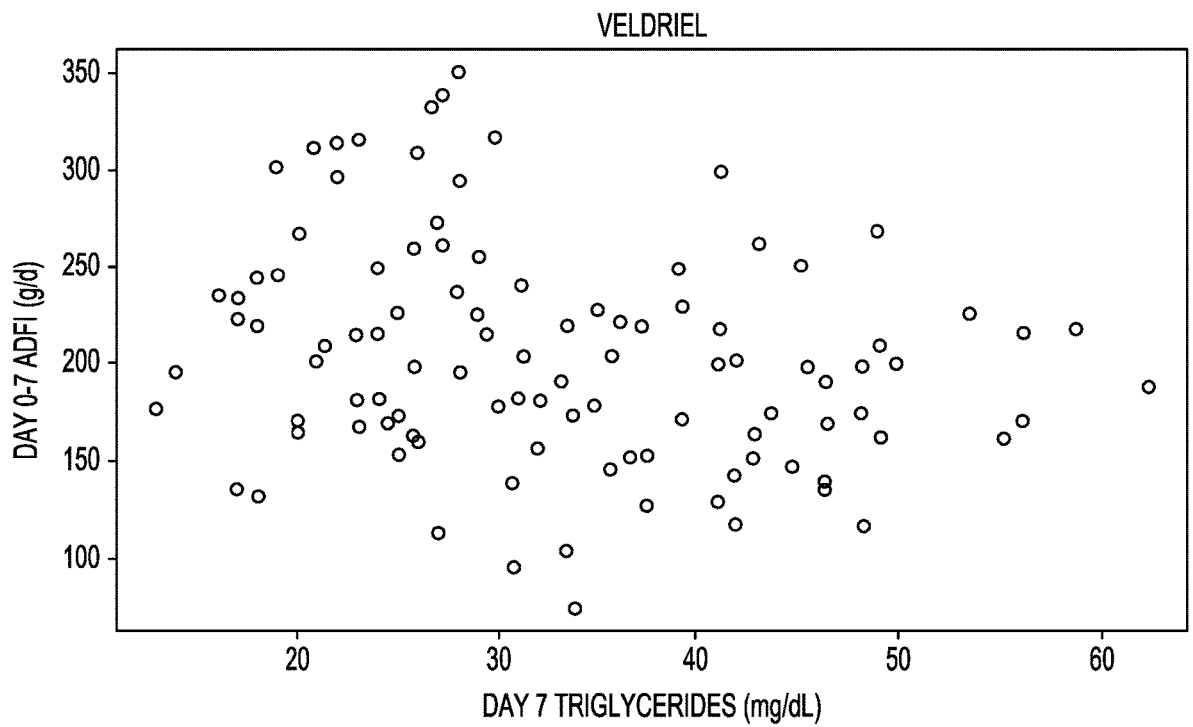
FIG. 2B illustrates day 0-8 ADFI versus day 7 triglyceride concentration, in accordance with various embodiments.
Figure 2C:
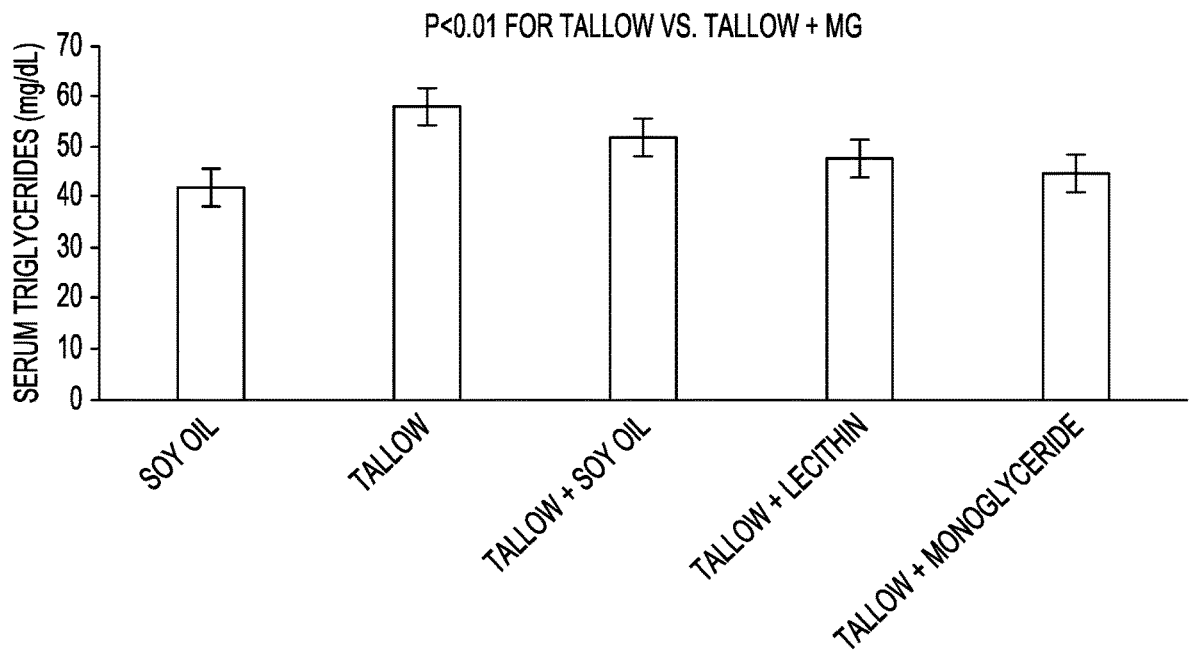
FIG. 2C illustrate serum triglyceride levels at day 7 for weaning pigs fed various diets, in accordance with various embodiments.
Figure 2D:
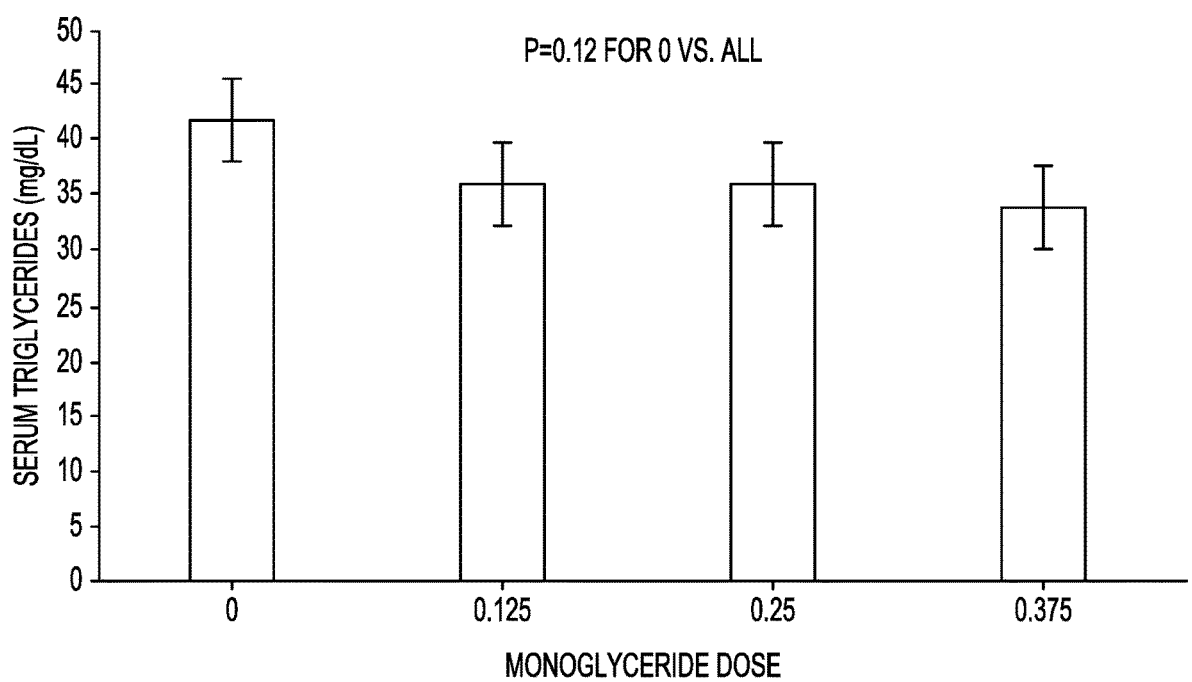
FIG. 2D illustrates serum triglyceride levels for weaning pigs fed various doses of monoglycerides, in accordance with various embodiments.

Example 6. The Effect of Two Monoglycerides on Blood Triglycerides and Cholecystokinin Trial designed to investigate the effect of two monoglycerides on blood triglycerides and cholecystokinin (CCK) to potentially find differences connected to beneficial metabolic effects. The first monoglyceride was >90% purity and the fatty acid profile is presented in Table 2 as Example 6. The second monoglyceride was glycerol monolaurate which is >90% glycerol monolaurate. This fatty acid profile is not presented in Table 2. No difference was detected in between the two types on monoglyceride or the dose. The monoglycerides lowered blood triglycerides. Higher concentrations of blood triglycerides were correlated with lower performance. Data is shown in FIGS. 2A-2D. FIGS. 2A and 1B illustrate day 0-8 ADFI versus day 7 triglyceride concentration for various weaned pigs. FIG. 2C illustrates serum triglyceride levels at day 7 for weaned pigs fed various diets. FIG. 2D illustrates serum triglyceride levels for pigs fed various doses of monoglycerides

Example 7. Monoglycerides with the Extrusion of Wheat

Trial designed to investigate monoglyceride use when included or not included in extrusion of wheat. The monoglyceride was >90% purity and the fatty acid profile is presented in Table 2 as Example 7. Monoglyceride did improve performance, but not when included in the extrusion process with wheat, which may have related to the extrusion process or to the use of extruded wheat in the diet.

Example 8. Dose Response of Monoglycerides

A 42-day trial with initial body weight of 5.6 kg used doses of 0, 0.2, 0.4, 0.6, 0.8 and 1.0% monoglyceride. The monoglyceride was >90% purity and the fatty acid profile is presented in Table 2 as Example 8. The diets contained antibiotics and high ZnO. Monoglyceride increased ADG and ADFI with increasing dose from 0-21 days post-weaning. The best treatment increased gain and intake by 25 and 11%, respectively. Inclusion of monoglyceride also dose-dependently decreased mortalities and mortality+removal.

Example 9. Testing Two Doses of Monoglyceride with a Source of MCFA

Trial was designed to investigate the effect of two doses of monoglyceride with or without inclusion of a source of medium chain fatty acids in triglyceride form. Monoglyceride was included at 0.2 or 0.4%. The monoglyceride was >90% purity and the fatty acid profile is presented in Table 2 as Example 9. Inclusion of both doses improved 0-21 day average daily gain and intake by 3.6 and 3.8%, respectively. No interactions on gain were detected from 0-21 days post-weaning with monoglyceride dose and MCFA.

Example 10. Monoglycerides from Palm Oil or Soy Oil

Trial was a blinded university trial in Brazil testing Cargill-made monoglycerides from either palm or soy oil. Two monoglycerides and their combinations were tested for a total inclusion of 0.4% of monoglyceride. These two monoglycerides are >90% purity and are presented in Table 2 Example 10 and labeled as MHS AP90 and MHS AS90. The MHS AP90 increased 0-14 d post-weaning gain and feed intake by 5.3 and 6.8%, respectively. No discernable difference was detected on intake and gain with MHS AS90 or the combination of monoglycerides. Additionally, the MHS AP90 increased insulin by ~30%.

Example 11. Analysis

Table 1 summarizes data from Examples 1-10.

TABLE 1

Summary of data from Examples 1-10.

| Example | Monoglyceride tested | Dose | Performance | Health |
|---|---|---|---|---|
| 1 | 1 | 0.5% | +6.1% ADG, +3.5% ADFI at 21 days, stronger response in soy vs. lard | NA |
| 2 | 1 | 0.25%, 0.5%, 1.0% | +18.5% ADG/ADFI at 0.25%, similar for 0.5% | NA |
| 3 | 3 | 0.25% | +3.8% ADG, +3.3% ADFI at 21 days. MG difference not detectable. | NA |
| 4 | 1 | 0.25% | −2.5% ADG, −1% ADFI at 21 days. Better response in palm vs. soy | NA |
| 5 | 1 | 0.15%, 0.25%, 0.4% | +21% ADG, +11% ADFI at 23.5 days. Biggest increment at 0.15% (+15%, +7%, respectively) | Linear reduction in mortality and removals from 13.5% to 6.75% at 42 days. Linear reduction in probability of veterinary treatments from 15.7 to 11.1%. |
| 6 | 2 | 0.125%, 0.25%, 0.375% | NA | NA |
| 7 | 1 | 0.25% | +4.8% ADG, + 4.1% ADFI at 21 days | NA |
| 8 | 1 | 0.2%, 0.4%, 0.6%, 0.8%, 1.0% | Quadratic, +25% ADG, +11% ADFI at 21 days for 1.0%, +22% ADG and +9% ADFI for 0.2% | Linear reduction in mortality and removal. From 8.8% to 6.12% at 41 days. |
| 9 | 1 | 0.2%, 0.4% | +3.9% ADG, 3.8% ADFI at 21 days for both doses | TBD |
| 10 | 3: MHS AP90 MHS AS90 50:50 AP90 and AS90 | 0.4%, 0.4%, 0.2% + 0.2% | ADG +7%, 1%, 3% ADFI +6%, 0%, 2% | NA |

Table 2 illustrates the fatty acid profiles of monoglycerides used in various Examples.

TABLE 2

Fatty acid profiles of monoglycerides of various Examples. For high confidence profiles, the fatty acid analysis has been confirmed. For medium confidence profiles, the material was not tested every time, but the batch was analyzed when received at the feed mill. For the low confidence profile Ex. 5, the animal results were similar to those from the other fatty acid profile Ex. 8 from same supplier used at the same location.

| Fatty acid | Ex. 1 | Ex. 2 | Ex. 3 | Ex. 4 | Ex. 5 | Ex. 6 | Ex. 7 | Ex. 8 | Ex. 9 | Ex. 10, MHS AP90 | Ex. 10, MHS AS90 |
|---|---|---|---|---|---|---|---|---|---|---|---|
| C16:0 | 11.53 | 11.53 | 11.53 | 11.53 | 11.10 | 57.3 | 57.3 | 11.10 | 10.4 | 37.48 | 57.75 |
| C16:1 | 0.06 | 0.06 | 0.06 | 0.06 | 0.23 | <0.01 | <0.01 | 0.23 | <0.01 | | |
| C18:0 | 56.78 | 56.78 | 56.78 | 56.78 | 47.5 | 40.5 | 40.5 | 47.5 | 87.3 | 54.57 | 40.23 |
| C18:1 | 26.61 | 26.61 | 26.61 | 26.61 | 33.2 | 0.04 | 0.04 | 33.2 | 0.9 | 7.09 | 0.71 |
| C18:2 | 3.3 | 3.3 | 3.3 | 3.3 | 7.1 | 0.08 | 0.08 | 7.10 | 0.07 | | |
| C18:3 | 0.17 | 0.17 | 0.17 | 0.17 | 0.65 | <0.01 | <0.01 | 0.65 | <0.01 | | |
| C18:4 | <0.01 | <0.01 | <0.01 | <0.01 | | <0.01 | <0.01 | | <0.01 | | |
| C20:0 | 0.55 | 0.55 | 0.55 | 0.55 | | 0.36 | 0.36 | | 0.56 | | |
| C20:1 | 0.11 | 0.11 | 0.11 | 0.11 | | <0.01 | <0.01 | | <0.01 | | |
| Other | 1.5 | 1.5 | 1.5 | 1.5 | | | | | | | |
| Confidence, H = high, M = medium, L = low | H | M | M | M | L | H | H | H | H | H | H |

Figure 3A:
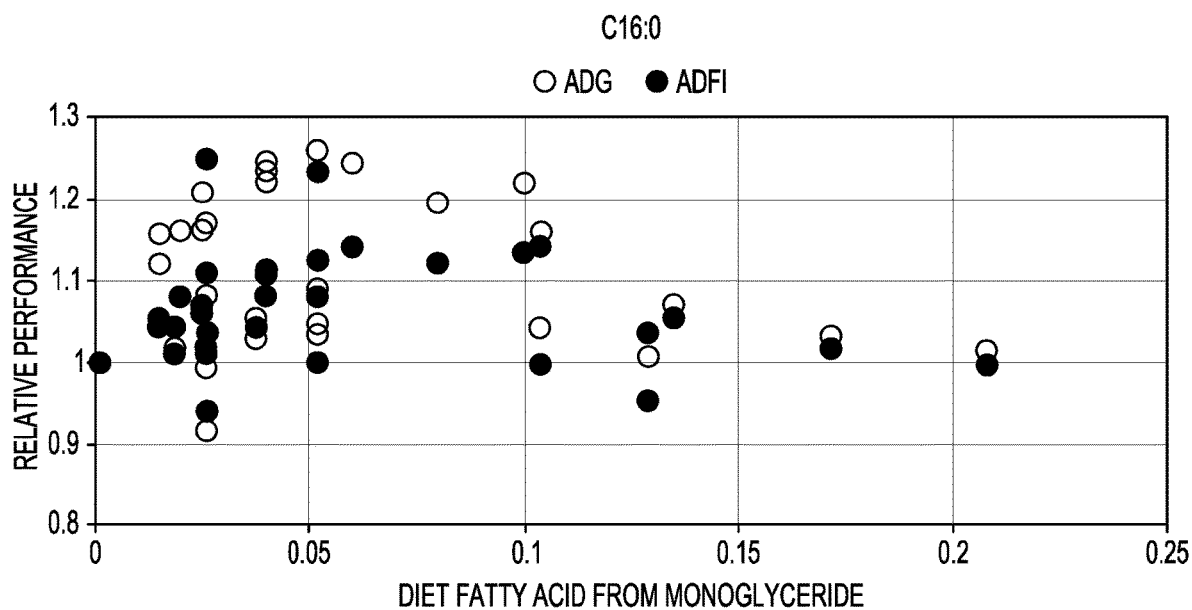
FIG. 3A illustrates the relative performance of various weaning pigs versus the percent of C16:0 monoglyceride in the diet, in accordance with various embodiments.
Figure 3B:
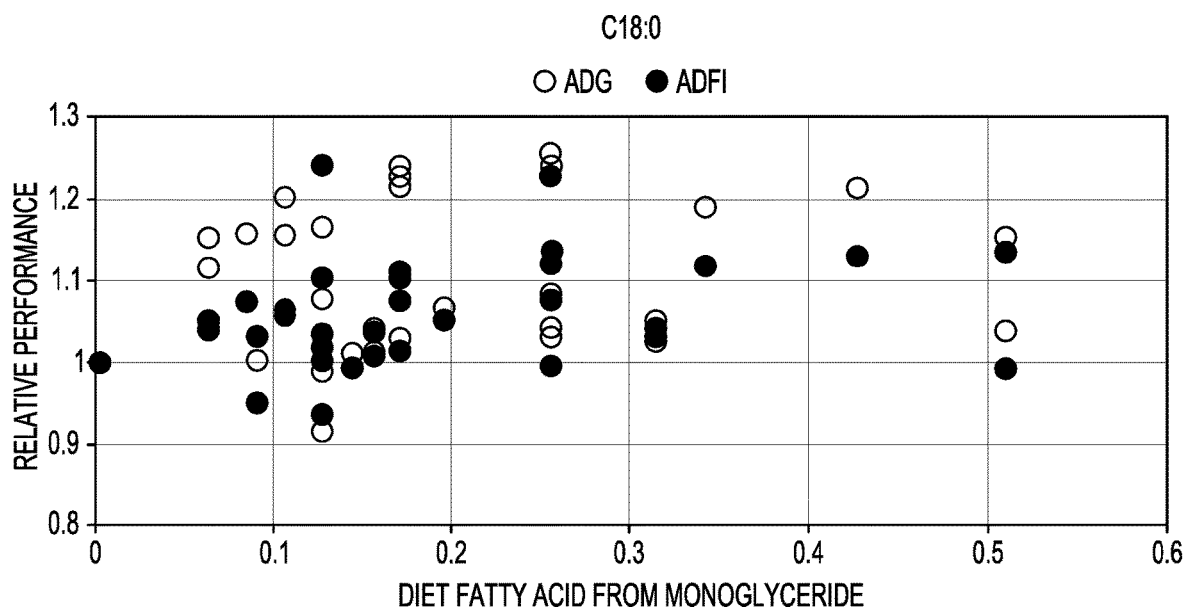
FIG. 3B illustrates the relative performance of various weaning pigs versus the percent of C18:0 monoglyceride in the diet, in accordance with various embodiments.
Figure 3C:
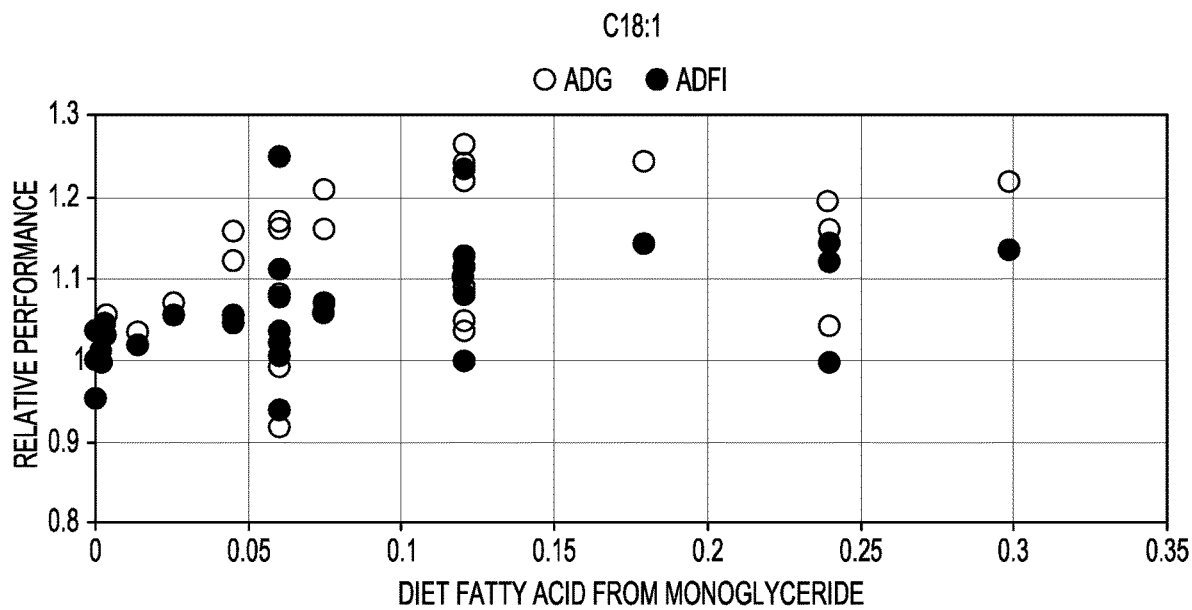
FIG. 3C illustrates the relative performance of various weaning pigs versus the percent of C18:1 monoglyceride in the diet, in accordance with various embodiments.
Figure 3D:
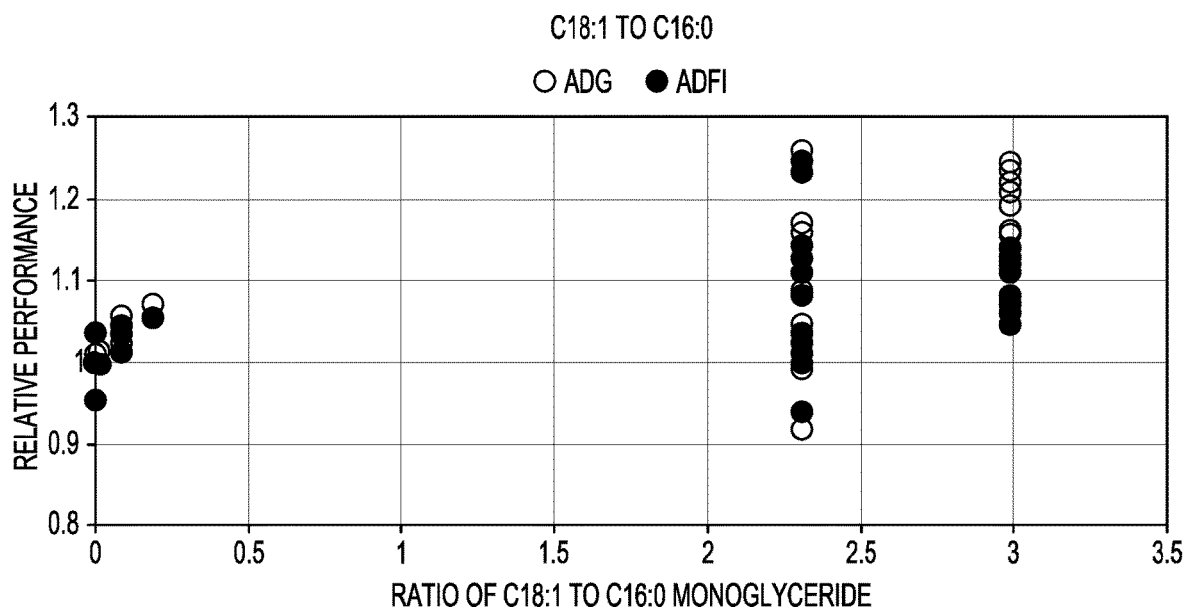
FIG. 3D illustrates the relative performance of various weaning pigs versus the ratio of C18:1 to C16:0 fatty acids from monoglycerides in the diet, in accordance with various embodiments.
Figure 3E:
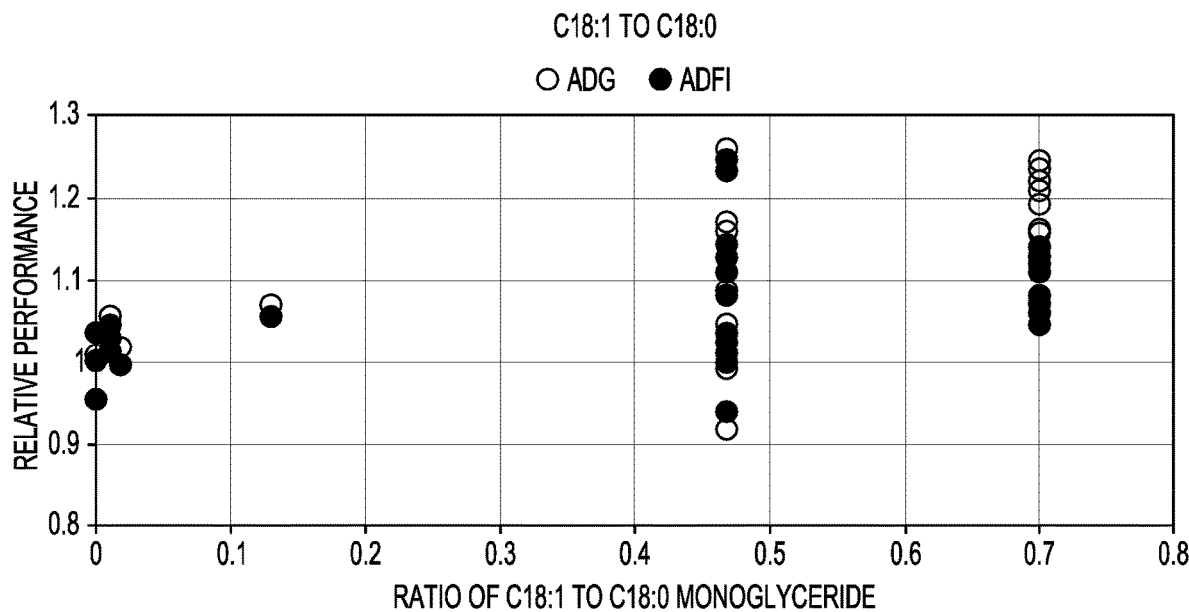
FIG. 3E illustrates the relative performance of various weaning pigs versus the ratio of C18:1 to C18:0 fatty acids from monoglycerides in the diet, in accordance with various embodiments.
Figure 3F:
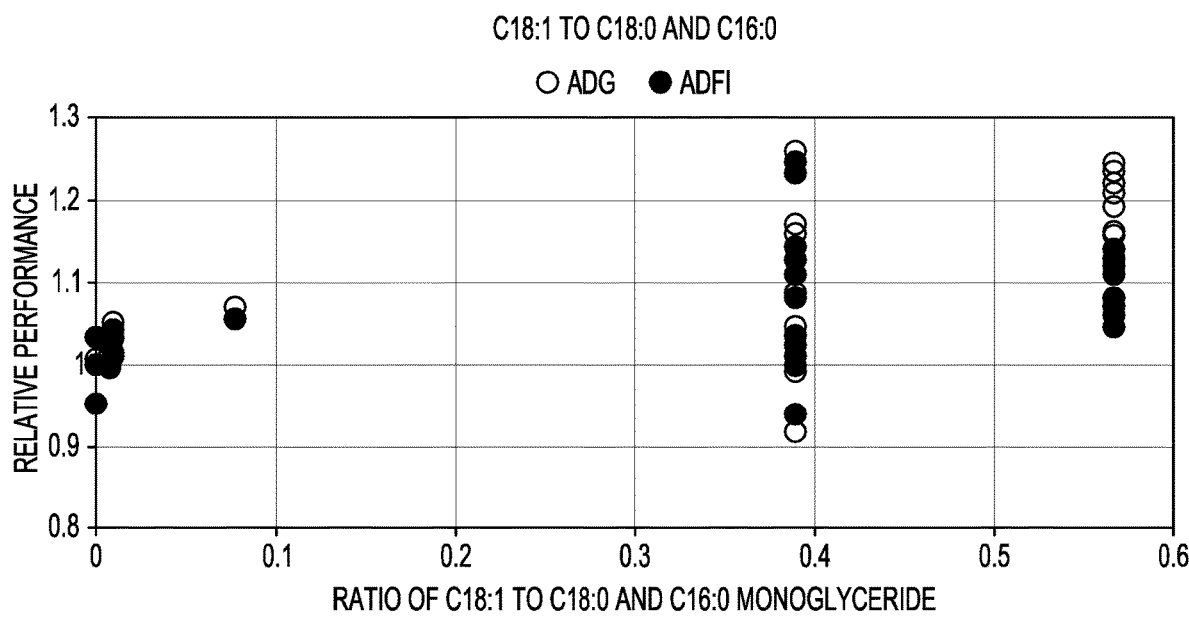
FIG. 3F illustrates the relative performance of various weaning pigs versus the ratio of C18:1 to C18:0 and C16:0 fatty acids from monoglycerides in the diet, in accordance with various embodiments.

FIGS. 3A-3C illustrate the relative performance of various weaning pigs versus the weight percent of C16:0, C18:0, or C18:1 monoglycerides in the diet, respectively, with data taken from Examples 1-5 and 7-10; Example 6 was omitted because it was designed with performance as an outcome. FIGS. 3D-3F illustrate the relative performance of various weaning pigs versus the weight ratio of C18:1 to C16:0, C18:1 to C18:0, or C18:1 to C18:0 and C16:0 fatty acids from monoglycerides in the diet, respectively, with data taken from Examples 1-5 and 7-10. The data shows a likely correlation between the presence of C18:1 monoglyceride in the diet and increased ADG and ADFI during weaning. The presence of C18:1 monoglycerides can correlate to increased concentrations of unsaturated monoglycerides and to increased iodine value.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a method of feeding an animal comprising: feeding the animal a diet comprising one or more monoglycerides.

Embodiment 2 provides the method of Embodiment 1, wherein a complete feed, a concentrate, a premix, a top dress, or a combination thereof, fed to the animal comprises the one or more monoglycerides in the animal's diet.

Embodiment 3 provides the method of Embodiment 2, wherein the complete feed is a daily feed ration.

Embodiment 4 provides the method of any one of Embodiments 1-3, wherein the method is a method of managing the animal.

Embodiment 5 provides the method of any one of Embodiments 1-4, wherein the method is a method of treating decreased average daily feed intake (ADFI) or decreased average daily gain (ADG) post-weaning.

Embodiment 6 provides the method of any one of Embodiments 1-5, wherein the method is a method of increasing activation of GPR119 receptors in the animal post-weaning.

Embodiment 7 provides the method of any one of Embodiments 1-6, wherein the method is a method of increasing insulin secretion in the animal post-weaning.

Embodiment 8 provides the method of any one of Embodiments 1-7, wherein the method is a method of improving intestinal function in the animal post-weaning.

Embodiment 9 provides the method of any one of Embodiments 1-8, wherein the animal is a ruminant, pig, poultry, horse, aquaculture, or wild game.

Embodiment 10 provides the method of any one of Embodiments 1-9, wherein the animal is a pig.

Embodiment 11 provides the method of any one of Embodiments 1-10, wherein the animal is a domestic pig, *Sus scrofa domesticus.*

Embodiment 12 provides the method of any one of Embodiments 1-11, wherein the animal is a breed of domestic pig comprising Aksai Black Pied, American Yorkshire, Angeln Saddleback, Appalachian English, Arapawa Island, Auckland Island Pig, Australian Yorkshire, Ba Xuyen, Babi Kampung, Bangur Pig, Bantu, Basque, Bazna, Beijing Black, Belarus Black Pied, Belgian Landrace, Bengali Brown Shannaj, Bentheim Black Pied, Berkshire, Bisaro, Black Canarian Pig, Black Slavonian, Breitovo, British Landrace, British Lop, British Saddleback, Bulgarian White, Cantonese, Celtic Pig, Chato Murciano, Chester White, Chiangmai Blackpig, Moodum Chiangmai, Creole Pig, Cumberland Pig, Czech Improved White, Danish Landrace, Danish Protest Pig, Dermantsi Pied, Dharane Kalo Sungur, Duroc, Dutch Landrace Pig, East Balkan Pig, Essex, Estonian Bacon, Fengjing Pig, Finnish Landrace, Forest Mountain, French Landrace, Gascon, German Landrace, Gloucestershire Old Spot, Grice, Guinea Hog, Göttingen Minipig, Hampshire, Hante, Hereford, Hezuo, Hogan Hog, Huntingdon Black Hog, Iberian, Italian Landrace, Japanese Landrace, Jeju Black Pig, Jinhua Pig, Juliana, Kakhetian, Kele Pig, Kemerovo, Korean Native Pig, Krskopolje, Kunekune, Lacombe, Large Black, Large Black-White, Large White, Latvian White, Leicoma, Li Yan Pig, Lincolnshire Curly-Coated Pig, Linderödssvin, Lithuanian Native, Lithuanian White, Livny, Malhado De Alcobaça, Mangalitsa, Meishan, Middle White, Minokawa Buta, Minzhu, Mong Cai, Mora Romagnola, Moura, Mukota, Mulefoot, Murom, Myrhorod, Neijiang, Nero Dei Nebrodi, Ningxiang, North Caucasian, North Siberian, Norwegian Landrace, Norwegian Yorkshire, Ossabaw Island, Oxford Sandy and Black, Pakchong 5, Philippine Native, Pietrain, Poland China, Red Wattle, Semirechensk, Siberian Black Pied, Small Black, Small White, Spots, Surabaya Babi, Swabian-Hall, Swedish Landrace, Taihu Pig, Tamworth, Thuoc Nhieu, Tibetan, Tokyo-X, Tsivilsk, Turopolje, Ukrainian Spotted Steppe, Ukrainian White Steppe, Urzhum, Vietnamese Potbelly, Welsh, Wessex Saddleback, West French White, Windsnyer, Wuzishan, Yanan, Yorkshire Blue and White, or a combination thereof.

Embodiment 13 provides the method of any one of Embodiments 1-12, wherein the method is a method of feeding a pig that is weaning, post-weaning, or a combination thereof.

Embodiment 14 provides the method of any one of Embodiments 1-13, wherein the animal is a pig, comprising feeding the pig the diet comprising the one or more monoglycerides from weaning to the end of nursery.

Embodiment 15 provides the method of any one of Embodiments 1-14, wherein the animal is a pig that is about just born to about 15 weeks old.

Embodiment 16 provides the method of any one of Embodiments 1-15, wherein the animal is a pig that is about just born to about 9 weeks old.

Embodiment 17 provides the method of any one of Embodiments 1-16, wherein the one or more monoglycerides are at least about 0.01 wt % of the animal's diet, of a daily feed ration fed to the animal, or a combination thereof.

Embodiment 18 provides the method of any one of Embodiments 1-17, wherein the one or more monoglycerides are about 0.01 wt % to about 10 wt % of the animal's diet, of a daily feed ration fed to the animal, or a combination thereof.

Embodiment 19 provides the method of any one of Embodiments 1-18, wherein the one or more monoglycerides are about 0.1 wt % to about 1% of the animal's diet, of a daily feed ration fed to the animal, or a combination thereof.

Embodiment 20 provides the method of any one of Embodiments 1-19, wherein the one or more monoglycerides are about 0.2 wt % to about 0.4 wt % of the animal's diet, of a daily feed ration fed to the animal, or a combination thereof.

Embodiment 21 provides the method of any one of Embodiments 1-20, wherein the animal is a pig and the one or more monoglycerides are about 20 to about 500 mg per kg of the pig's mass per day.

Embodiment 22 provides the method of any one of Embodiments 1-21, wherein the animal is a pig and the one or more monoglycerides are about 40 to about 250 mg per kg of the pig's mass per day.

Embodiment 23 provides the method of any one of Embodiments 1-22, wherein the animal's diet comprises soy oil, palm oil, tallow, lecithin, diglycerides, triglycerides, or a combination thereof.

Embodiment 24 provides the method of any one of Embodiments 1-23, wherein the animal's diet, a daily feed ration fed to the animal comprising the one or more monoglycerides, or a combination thereof, is substantially free of palm oil.

Embodiment 25 provides the method of any one of Embodiments 1-24, wherein the one or more monoglycerides are chosen from glycerol propionate (propanoate, C3:0), butyrate (butanoate, C4:0), valerate (pentanoate, C5:0), caproate (hexanoate, C6:0), enanthate (heptanoate, C7:0), caprylate (octanoate, C8:0), pelargonate (nonanoate, C9:0), caprate (decanoate, C10:0), undecylate (undecanoate, C11:0), laurate (dodecanoate, C12:0), tridecylate (tridecanoate, C13:0), myristate (tetradecanoate, C14:0), pentadecylate (pentadecanoate, C15:0), palmitate (hexadecanoate, C16:0), margarate (heptadecanoate, C17:0), stearate (octadecenoate, C18:0), nonadecylate (nonadecanoate, C19:0), arachidate (eicosanoate, C20:0), heneicosylate (heneicosanoate, C21:0), behenate (docosanoate, C22:0), tricosylate (tricosanoate, C23:0), lignocerate (tetracosanoate, C24:0), pentacosylate (pentacosanoate, C25:0), cerotate (hexacosanoate, C26:0), heptacosylate (heptacosanoate, C27:0), montanate (octacosanoate, C28:0), nonacosylate (nonacosanoate, C29:0), melissate (triacontanoate, C30:0), henatriacontylate (henatriacontanoate, C31:0), lacceroate (dotriacontanoate, C32:0), psyllate (tritriacontanoate, C33:0), geddate (tetratriacontanoate, C34:0), ceroplastate (pentatriacontanoate, C35:0), hexatriacontylate (hexatriacontanoate, C36:0), heptatriacontanoate (heptatriacontanoate, C37:0), octatriacontanoate (octatriacontanoate, C38:0), α-linolenate (C18:3), stearidonate (C18:4), eicosapentaenoate (C20:5), docosahexaenoate (C22:6), linoleate (C18:2), linolelaidate (C18:2), γ-linolenate (C18:3), dihomo-γ-linolenate (C20:3), arachidonate (C20:4), docosatetraenoate (C22:4), palmitoleate (C16:1), vaccenate (C18:1), paullinate (C20:1), oleate (C18:1), elaidate (C18:1), gondoate (C20:1), erucate (C22:1), nervonate (C24:1), mead acid ester (C20:3), and a combination thereof.

Embodiment 26 provides the method of any one of Embodiments 1-25, wherein the one or more monoglycerides are chosen from glycerol stearate, palmitate, oleate, linoleate, laurate, and a combination thereof.

Embodiment 27 provides the method of any one of Embodiments 1-26, wherein the one or more monoglycerides are non-antimicrobial.

Embodiment 28 provides the method of any one of Embodiments 1-27, wherein the animal's feed ration, the animal's diet, or a combination thereof, is substantially free of antimicrobial monoglycerides.

Embodiment 29 provides the method of any one of Embodiments 1-28, wherein the one or more monoglycerides are at least about 90 wt % monoglycerides.

Embodiment 30 provides the method of any one of Embodiments 1-29, wherein the one or more monoglycerides are at least about 95 wt % monoglycerides.

Embodiment 31 provides the method of any one of Embodiments 1-30, wherein one or more monoglycerides comprising stearate (octadecenoate, C18:0) are about 0 wt % to about 5 wt % of the animal's diet, of a daily feed ration fed to the animal, or a combination thereof.

Embodiment 32 provides the method of any one of Embodiments 1-31, wherein one or more monoglycerides comprising stearate (octadecenoate, C18:0) are about 0.05 wt % to about 0.6 wt % of the animal's diet, of a daily feed ration fed to the animal, or a combination thereof.

Embodiment 33 provides the method of any one of Embodiments 1-32, wherein one or more monoglycerides comprising oleate (C18:1) are about 0 wt % to about 5 wt % of the animal's diet, of a daily feed ration fed to the animal, or a combination thereof.

Embodiment 34 provides the method of any one of Embodiments 1-33, wherein one or more monoglycerides comprising oleate (C18:1) are about 0.01 wt % to about 0.3 wt % of the animal's diet, of a daily feed ration fed to the animal, or a combination thereof.

Embodiment 35 provides the method of any one of Embodiments 1-34, wherein one or more monoglycerides comprising oleate (C18:1) are about 0.02 wt % to about 0.25 wt % of the animal's diet, of a daily feed ration fed to the animal, or a combination thereof.

Embodiment 36 provides the method of any one of Embodiments 1-35, wherein one or more monoglycerides comprising palmitate (hexadecanoate, C16:0) are about 0 wt % to about 5 wt % of the animal's diet, of a daily feed ration fed to the animal, or a combination thereof.

Embodiment 37 provides the method of any one of Embodiments 1-36, wherein one or more monoglycerides comprising palmitate (hexadecanoate, C16:0) are about 0.01 wt % to about 0.25 wt % of the animal's diet, of a daily feed ration fed to the animal, or a combination thereof.

Embodiment 38 provides the method of any one of Embodiments 1-37, wherein the animal's diet, a daily feed ration fed to the animal, or a combination thereof, has a weight ratio of C18:1 monoglycerides to C16:0 monoglycerides of about 0 to about 20.

Embodiment 39 provides the method of any one of Embodiments 1-38, wherein the animal's diet, a daily feed ration fed to the animal, or a combination thereof, has a weight ratio of C18:1 monoglycerides to C16:0 monoglycerides of about 2 to about 3.5.

Embodiment 40 provides the method of any one of Embodiments 1-39, wherein the animal's diet, a daily feed ration fed to the animal, or a combination thereof, has a weight ratio of C18:1 monoglycerides to C18:0 monoglycerides of about 0 to about 20.

Embodiment 41 provides the method of any one of Embodiments 1-40, wherein the animal's diet, a daily feed ration fed to the animal, or a combination thereof, has a weight ratio of C18:1 monoglycerides to C18:0 monoglycerides of about 0.01 to about 0.7.

Embodiment 42 provides the method of any one of Embodiments 1-41, wherein the animal's diet, a daily feed ration fed to the animal, or a combination thereof, has a weight ratio of C18:1 monoglycerides to C18:0 and C16:0 monoglycerides of about 0 to about 20.

Embodiment 43 provides the method of any one of Embodiments 1-42, wherein the animal's diet, a daily feed ration fed to the animal, or a combination thereof, has a weight ratio of C18:1 monoglycerides to C18:0 and C16:0 monoglycerides of about 0.01 to about 0.6.

Embodiment 44 provides the method of any one of Embodiments 1-43, wherein the animal's diet, a daily feed ration fed to the animal, or a combination thereof, further comprises antimicrobials, antibiotics, a zinc additive, or a combination thereof.

Embodiment 45 provides the method of any one of Embodiments 1-44, wherein the animal's diet comprises a daily feed ration comprising the one or more monoglycerides, wherein the daily feed ration is in the form of a pellet, a mash, an extruded food, an expanded food, or a combination thereof.

Embodiment 46 provides the method of any one of Embodiments 1-45, wherein the animal's diet comprises a daily feed ration, wherein the daily feed ration is a complete feed comprising a base animal feed and a premix, concentrate, or top dress that comprises the one or more monoglycerides.

Embodiment 47 provides the method of any one of Embodiments 1-46, wherein the one or more monoglycerides increases activation of GPR119 receptors in the animal.

Embodiment 48 provides the method of any one of Embodiments 1-47, wherein the one or more monoglycerides increase insulin secretion in the animal, decreasing blood glucose and blood triglycerides.

Embodiment 49 provides the method of any one of Embodiments 1-48, wherein the method causes greater average daily feed intake (ADFI) post-weaning, greater average daily gain (ADG) post-weaning, fewer veterinary treatments post-weaning, reduced mortality and decreased removals post-weaning, or a combination thereof, as compared to a method that is otherwise the same but comprises feeding the animal less of the one or more monoglycerides.

Embodiment 50 provides a method of feeding a post-weaning pig comprising:
feeding the post-weaning pig a diet comprising one or more monoglycerides comprising oleate (C18:1), to increase the activation of GPR119 receptors in the pig, to increase average daily feed intake, and to increase average daily gain, wherein the C18:1 monoglycerides are about are about 0.01 wt % to about 5 wt % of the animal's diet, of a daily feed ration fed to the animal, or a combination thereof.

Embodiment 51 provides a concentrate, premix, or top dress for animals comprising:
one or more monoglycerides comprising oleate (C18:1), wherein the weight ratio of C18:1 monoglycerides to C18:0 and C16:0 monoglycerides is at least about 0.01.

Embodiment 52 provides the concentrate, premix, or top dress of Embodiment 51, wherein the weight ratio of C18:1 monoglycerides to C18:0 and C16:0 monoglycerides is at least about 0.01 to about 20.

Embodiment 53 provides the concentrate, premix, or top dress of any one of Embodiments 51-52, wherein the weight ratio of C18:1 monoglycerides to C18:0 and C16:0 monoglycerides is at least about 0.01 to about 0.6.

Embodiment 54 provides the concentrate, premix, or top dress of any one of Embodiments 51-53, wherein the premix is a feed additive.

Embodiment 55 provides the concentrate or top dress of any one of Embodiments 51-54, wherein the concentrate or top dress is for direct administration to the animals.

Embodiment 56 provides a complete feed for animals comprising:
one or more monoglycerides comprising oleate (C18:1), wherein the one or more monoglycerides comprising oleate (C18:1) are about 0.01 wt % to about 5 wt % of the complete feed.

Embodiment 57 provides the complete feed of Embodiment 56, comprising:
the concentrate, premix, or top dress of any one of Embodiments 51-55; and a base animal feed.

Embodiment 58 provides the complete feed of any one of Embodiments 56-57, wherein the one or more monoglycerides comprising oleate (C18:1) are about 0.01 wt % to about 5 wt % of the complete feed.

Embodiment 59 provides the complete feed of any one of Embodiments 56-58, wherein one or more monoglycerides comprising oleate (C18:1) are about 0.01 wt % to about 0.3 wt % of the complete feed.

Embodiment 60 provides the complete feed of any one of Embodiments 56-59, wherein one or more monoglycerides comprising oleate (C18:1) are about 0.02 wt % to about 0.25 wt % of the complete feed.

Embodiment 61 provides the complete feed of any one of Embodiments 56-60, wherein the complete feed is ruminant feed, pig feed, poultry feed, equine feed, aquaculture feed, wild game feed, or a combination thereof.

Embodiment 62 provides the complete feed of any one of Embodiments 56-61, wherein the complete feed is a pig feed composition.

Embodiment 63 provides the complete feed of any one of Embodiments 56-62, wherein the complete feed is a pig feed for weaning pigs.

Embodiment 64 provides a method of making the complete feed of any one of Embodiments 56-63, the method comprising:
combining the concentrate, premix, or top dress of any one of Embodiments 51-55 with the base animal feed to form the complete feed.

Embodiment 65 provides the method, concentrate, premix, top dress, or complete feed of any one of Embodiments 1-64 optionally configured such that all elements or options recited are available to use or select from.

What is claimed is:

1. A method of feeding a pig comprising:
feeding the pig a diet comprising one or more monoglycerides;
wherein the one or more monoglycerides are 0.1 wt % to 1 wt % of the pig's diet, of a daily feed ration fed to the pig, or a combination thereof; and
wherein the pig is weaning, post-weaning, or a combination thereof.

2. The method of claim 1, wherein a complete feed, a concentrate, a premix, a top dress, or a combination thereof, fed to the pig comprises the one or more monoglycerides in the animal pig's diet.

3. The method of claim 1, comprising feeding the pig the diet comprising the one or more monoglycerides from weaning to the end of nursery.

4. The method of claim 1, wherein the one or more monoglycerides are 0.2 to 0.4 wt % of the animal's diet, of a daily feed ration fed to the animal, or a combination thereof.

5. The method of claim 1, wherein the one or more monoglycerides are chosen from glycerol stearate, palmitate, oleate, linoleate, laurate, and a combination thereof.

6. The method of claim 1, wherein the one or more monoglycerides are non-antimicrobial.

7. The method of claim 1, wherein the pig's feed ration, the pig's diet, or a combination thereof, is substantially free of antimicrobial monoglycerides.

8. The method of claim 1, wherein one or more monoglycerides comprising oleate (C18:1) are about 0 wt % to about 5 wt % of the pig's diet, of a daily feed ration fed to the pig, or a combination thereof.

9. The method of claim 1, wherein one or more monoglycerides comprising oleate (C18:1) are about 0.02 wt % to about 0.25 wt % of the pig's diet, of a daily feed ration fed to the pig, or a combination thereof.

10. The method of claim 1, wherein the pig's diet, a daily feed ration fed to the pig, or a combination thereof, has a weight ratio of C18:1 monoglycerides to C18:0 and C16:0 monoglycerides of about 0.01 to about 0.6.

11. The method of claim 1, wherein the pig's diet comprises a daily feed ration comprising the one or more monoglycerides, wherein the daily feed ration is in the form of a pellet, a mash, an extruded food, an expanded food, or a combination thereof.

12. The method of claim 1, wherein the one or more monoglycerides increases activation of GPR119 receptors in the pig.

13. The method of claim 1, wherein the one or more monoglycerides increase insulin secretion in the pig, decreasing blood glucose and blood triglycerides.

14. The method of claim 1, wherein the method causes greater average daily feed intake (ADFI) post-weaning, greater average daily gain (ADG) post-weaning, fewer veterinary treatments post-weaning, reduced mortality and decreased removals post-weaning, or a combination thereof, as compared to a method that is otherwise the same but comprises feeding the pig less of the one or more monoglycerides.

* * * * *